United States Patent [19]

Steinmetz et al.

[11] Patent Number: 4,885,384

[45] Date of Patent: Dec. 5, 1989

[54] PROCESS FOR THE CARBONYLATION OF IODOAROMATIC COMPOUNDS

[76] Inventors: Guy R. Steinmetz, 835 Sir Echo Dr.; Kevin J. Edgar, 1010 Olympus Cir.; Stephen N. Falling, 225 Woodstock Pl., all of Kingsport, Tenn. 37663

[21] Appl. No.: 168,050

[22] Filed: Mar. 14, 1988

[51] Int. Cl.$^4$ .............................................. C07C 51/10
[52] U.S. Cl. .................... 562/406; 562/473; 562/475; 562/477; 562/480; 562/493; 568/797
[58] Field of Search ................ 568/775, 797; 562/406, 562/493, 473, 475, 477, 480

[56] References Cited

U.S. PATENT DOCUMENTS

| | | | |
|---|---|---|---|
| 3,733,354 | 5/1973 | Cassar et al. | 562/406 |
| 3,988,358 | 10/1976 | Heck | 260/465 |
| 4,060,547 | 11/1977 | Paulik et al. | 560/204 |
| 4,649,216 | 3/1987 | Rule et al. | 562/406 |
| 4,705,890 | 11/1987 | Steinmetz et al. | 562/406 |

FOREIGN PATENT DOCUMENTS 206543 12/1985 European Pat. Off. .

*Primary Examiner*—Werren B. Lone
*Assistant Examiner*—Vera C. Clarke
*Attorney, Agent, or Firm*—Charles R. Martin; William P. Heath, Jr.

[57] ABSTRACT

A process for the production of aromatic carboxylic acids which comprises carbonylating substituted iodoaromatic compounds in the presence of carbon monoxide, a catalytic amount of a transition metal catalyst, and a Bronsted base in a mixture of a carboxylic acid and water under aromatic carboxylic acid forming conditions of temperature and pressure.

14 Claims, No Drawings

PROCESS FOR THE CARBONYLATION OF IODOAROMATIC COMPOUNDS

BACKGROUND OF THE INVENTION

1. Field of the Invention

This invention relates to the preparation of aromatic acids by the carbonylation of iodoaromatic compounds. The carbonylation is conducted in the presence of a Bronsted base, a mixture of water and a carboxylic acid, and a transition metal catalyst.

2. Discussion of the Background

The carbonylation of aromatic halides to obtain aromatic carboxylic acids and esters is well known. For example, U.S. Pat. No. 3,988,358 discloses the carbonylation of aromatic halides in the presence of an alcohol and a tertiary amine to produce the corresponding carboxylic acid ester. This reference further discloses that changes in the reaction solvent have little effect on product composition.

SUMMARY OF THE INVENTION

One object of the present invention is to provide a process for the preparation of aromatic acids, particularly hydroxyaromatic acids which can be performed on an industrial scale using inexpensive reactants.

Another object of the invention is to provide a process which produces aromatic acids in high yields with relatively small amounts of side products.

These and other objects of the invention, which will become apparent from the following specification, have been achieved by the present process for the production of aromatic carboxylic acids which comprises carbonylating aromatic iodides in the presence of carbon monoxide, a catalytic amount of a transition metal catalyst, and a Bronsted base in a carboxylic acid/water medium under aromatic carboxylic acid forming conditions of temperature and pressure.

DETAILED DESCRIPTION OF THE PREFERRED EMBODIMENTS

In accordance with the present invention, it has now been found that iodoaromatic compounds can be carbonylated to aromatic carboxylic acids in high yields by reaction with carbon monoxide in the presence of a metal catalyst and a Bronsted base in a carboxylic acid/water medium. In contrast it has been found that if the carbonylation is conducted in a carboxylic acid solvent such as acetic acid with no added water, incomplete conversion of the substituted iodoaromatic compound is observed. It has been disclosed in U.S. Pat. No. 3,988,358 that carbonylation of haloaromatic compounds is not solvent dependent. However, we have discovered that the carbonylation of iodoaromatics, such as p-iodophenol, is very solvent dependent which was not recognized in the prior art. For example, carbonylation of p-iodophenol in an acetic acid solvent results in reduction to phenol as the primary reaction product with poor conversion to p-hydroxybenzoic acid as the carbonylation product. If the carbonylation is conducted in a mixed acetic acid/water solvent, complete carbonylation of the iodoaromatic to high yields of aromatic acid was observed with only small amounts of the reduction product.

Consistent with the above observation that these carbonylations are solvent dependent is the disclosure in European Patent Application 206,543 that coupling of the haloaromatic is observed when only water is used as the solvent under similar reaction conditions. No coupling products have been observed when a carboxylic acid/water medium has been used as a carbonylation solvent. Disclosures in both U.S. Pat. No. 3,988,358 and European Patent Application No. 206,543 illustrate that use of a mixture of water and a carboxylic acid claimed in this invention is unobvious in the carbonylation of iodoaromatic compounds to their respective aromatic acids.

Iodinated aromatic compounds which can be utilized in the practice of the present invention are any unsubstituted or substituted iodoaromatic compounds, particularly hydroxyaromatic iodides. Suitable iodinated aromatic compounds include hydrocarbon iodoaromatics, nitrogen-containing iodoaromatics, oxygen-containing iodoaromatics, and sulfur-containing iodoaromatics. Typical hydrocarbon aromatics include iodophenol and iodinated condensed ring aromatics such as iodonaphthol. Typical sulfur-containing aromatics are, for example, iodinated hydroxy- and amino-thiophene and benzothiophene. Typical nitrogen-containing aromatics include iodinated anilines and iodinated hydroxyanilines, pyridines and quinolines. The iodoaromatic compounds may be further substituted with ether, carbonyl and sulfide groups if desired.

The iodoaromatic starting materials may be substituted by one or more alkyl groups, preferably alkyl groups having from 1–6 carbon atoms. Especially preferred alkyl groups are methyl, ethyl, propyl, and butyl groups.

Additional substituents may be present in the iodoaromatic compound. Such groups include phenyl, chloro, fluoro, bromo, nitro and $C_{1-6}$ alkoxy groups as well as aryl sulfones and aryl ketones. Preferred starting materials are iodinated phenolic compounds, i.e., hydroxybenzenes and hydroxynaphthalenes. Examples of particularly preferred phenolic compounds include iodinated derivatives of: phenol, 2-methylphenol, 4-methylphenol, 2,6-dimethylphenol, 1-naphthol, 2-naphthol, 4-nitrophenol, 2-iodophenol, 4-hydroxybenzoic acid, 4-chlorophenol, 2-chlorophenol, 3-ethylphenol and 2-methoxyphenol. Also particularly preferred are iodinated derivatives of: 2-hydroxypyridine, 3-hydroxypyridine, 8-hydroxyquinoline, 2-phenylphenol, 4-phenylphenol, and aniline.

In the process of the invention, the iodoaromatic compound is carbonylated in a mixture of water and a carboxylic acid. Suitable carboxylic acids are aliphatic and aromatic carboxylic acids having 2–12 carbon atoms. Specific examples include acetic acid, propionic acid, butyric acid, benzoic acid and mixtures thereof, with acetic acid being most preferred.

The ratio of water to acid can be adjusted to correspond to the desired product whether the product results from reduction, carbonylation or coupling as noted above.

The transition metal catalyst can be palladium, rhodium, nickel or ruthenium, preferably palladium.

The palladium catalyst can be provided to the reaction medium as either palladium metal or as any of a number of palladium salts or complexes, such as palladium acetate. The amount of palladium is not significant as long as enough is present to catalyze the reaction. Preferably, the catalyst is present in a concentration of 1 to 0.0001 mole percent, preferably 0.025 to 0.001 mole percent, based on the moles of iodoaromatic reactant. Therefore, the total reaction medium has a catalyst concentration of about 1000 ppm to 0.1 ppm with preferred catalyst concentrations of 250 to 1 ppm.

The rhodium catalyst can be provided to the reaction medium as either rhodium metal or as any of a number of rhodium salts or complexes. Illustrative sources of rhodium are rhodium trichloride, rhodium tribromide, rhodium triiodide, rhodium acetate, rhodium oxide, dicarbonyl rhodium acetylacetonate, rhodium carbonyl complexes and their phosphine and halogen substituted analogs. The amount of rhodium is not significant as long as enough is present to catalyze the reaction. Preferably, the catalyst is present in a concentration of 10 to 0.001 mole percent, preferably 1.0 to 0.01 mole percent, based on the moles of iodoaromatic reactant. Therefore, the total reaction medium has a catalyst concentration of about 10,000 ppm to 10 ppm with preferred catalyst concentrations of 1000 to 100 ppm.

The nickel catalyst can be provided to the reaction medium as either nickel metal or as any of a number of nickel salts or complexes, such as nickel iodide. The amount of nickel is not significant as long as enough is present to catalyze the reaction. Preferably, the catalyst is present in a concentration of 10 to 0.001 mole percent, preferably 2.5 to 0.1 mole percent, based on the moles of iodoaromatic reactant. Therefore, the total reaction medium has a catalyst concentration of about 10,000 ppm to 1 ppm with preferred catalyst concentrations of 1,000 to 100 ppm.

The ruthenium catalyst can be provided to the reaction medium as any of a number of ruthenium salts or complexes that are capable of providing ruthenium in a soluble form in the reaction. Illustrative sources of ruthenium are ruthenium trichloride, ruthenium tribromide, ruthenium triiodide, ruthenium acetate, ruthenium acetylacetonate, ruthenium dioxide, ruthenium tetraoxide, ruthenium pentacarbonyl and dodecacarbonyltriruthenium and their phosphine and halogen substituted analogs. The amount of ruthenium is not significant as long as enough is present to catalyze the reaction. Preferably, the catalyst is present in a concentration of 10 to 0.01 mole percent, preferably 1.0 to 0.1 mole percent, based on the moles of iodoaromatic reactant. Therefore, the total reaction medium has a catalyst concentration of about 10,000 ppm to 10 ppm with preferred catalyst concentrations of 1000 to 100 ppm.

A Bronsted base is also added to the carboxylic acid reaction medium to maintain and enhance the reaction rate of the carbonylation process. By the term "Bronsted base" is meant any substance that can act as a proton acceptor in the reaction medium. In particular, the Bronsted base can be an acetate, formate, hydroxide, carbonate or alkoxide of an alkali, alkaline earth, transition or non-transition metal. For each mole equivalent of aromatic acid produced, one mole equivalent of the Bronsted base is required. Amounts of Bronsted base in excess of that amount can also be added.

Examples of a Bronsted base are alkali metal carbonates, such as lithium carbonate, as well as alkali metal acetates such as lithium acetate, sodium acetate, potassium acetate and the like, preferably lithium acetate. Alkaline earth metal acetates, such as magnesium acetate, can also be used. Transition and non-transition metal acetates such as iron, manganese, zinc and tin acetates can also be used. Amines such as pyridines and trialkylamines, for example triethylamine or trimethylamine, can also be used. Alkali metal acetates can be generated in situ by adding an alkali metal component, such as lithium carbonate, to the carboxylic acid reaction medium such as acetic acid, to form lithium acetate. Also alkyl acetates, such as methyl acetate, can be used when in the presence of an alkali or alkaline earth metal iodide. Alkyl acetates can also be generated in situ by adding an alkanol, such as methanol, to the reaction medium which can subsequently react with the carboxylic acid solvent to form the alkyl acetate.

An alkali or alkaline earth metal iodide which functions as an iodide promoter may optionally be added to the carboxylic acid reaction medium to enhance the carbonylation rate of the carbonylation process. By the term "iodide promoter" is meant an alkali or alkaline earth metal iodide that is capable of providing a soluble form of iodide in the reaction as any number of salts or complexes. Illustrative examples are alkali metal iodides such as lithium iodide, sodium iodide, potassium iodide, rubidium iodide and alkaline earth iodides such as magnesium diiodide, calcium diiodide, strontium diiodide and barium diiodide. The iodide promoter can be added in an amount of about 0.5 to 26 weight percent based on the amount of the carboxylic acid reaction medium, preferably 5 to 15 weight percent.

The carbonylation reaction is conducted in the presence of carbon monoxide which is employed in amounts such that the total reaction pressure is suitable for the formation of the aromatic carboxylic acid. The carbon monoxide employed may be essentially pure or it may contain other gases such as carbon dioxide, hydrogen, methane and other compounds produced by synthesis gas plants. Normally, the carbon monoxide will be at least 90, preferably at least 95 percent pure.

The process of the present invention can be conducted at temperatures and pressures suitable for formation of the aromatic carboxylic acid. The temperatures and pressures are interdependent and can vary considerably. While the process can be carried out at pressures as high as 10,000 psig, the cost of utilities and equipment required for such high pressure operation cannot normally be commercially justified. Thus, the pressure normally will be in the range of about 10 to 4000 psig, preferably about 300 to 1500 psig. While temperatures as low as 50° C. and higher than 225° C. may be used, the process normally is carried out between about 50° to 225° C. The preferred temperature range is 100° to 175° C.

The process of the present invention is particularly useful for the preparation of aromatic carboxylic acids such as p-hydroxybenzoic acid which may be used in the preparation of liquid crystalline polymers.

The process of the invention can be carried out as a batch, semi-continuous or continuous operation. In the manufacture of aromatic carboxylic acids in the quantities required for use in the preparation of polymers, the process described hereinabove will be carried out in a continuous manner. A typical continuous method of practicing the invention comprises feeding into a mixed pressure vessel a liquid stream composed of the iodoaromatic compound in acetic acid/water, the metal catalyst, the Bronsted base, the iodide promoter if desired, and a gaseous stream of carbon monoxide. The pressure vessel is equipped with a means for maintaining the desired temperature and pressure. The liquid mixture from the reactor column is cooled until the aromatic acid precipitates and is separated from the solution. The iodide salt produced from the carbonylation can then be recycled as a reactant feed stock for other process reactions. Although the iodide salt can be recycled to any desired process, it is preferred to recycle the iodide salt to an iodination reaction for the preparation of the iodinated hydroxy- and aminoaromatic starting materials which are used in the present carbonylation process. A particularly preferred iodination process is the aqueous iodination of hydroxyaromatic and aminoaromatic compounds disclosed in copending application Ser. No. 086,478, filed Aug. 18, 1987. The disclosure of this application is incorporated herein by reference for a more complete appreciation of this iodination process. In such a manner, the iodination/carbonylation reaction can be run in a continuous process with little loss of iodine in the complete reaction cycle.

Other features of the invention will become apparent in the course of the following descriptions of exemplary embodiments which are given for illustration of the invention and are not intending to be limiting thereof.

EXAMPLES

Our invention is further illustrated by the following examples. In the procedures utilized in the examples, the materials employed are loaded onto a 330 mL autoclave constructed of Hastelloy B2 alloy which is designed to operate in a rocking mode. The autoclave is pressurized with 500 psig carbon monoxide gas pressure at room temperature and then the gas is vented and the autoclave is sealed. In these examples the autoclave is pressurized to 200 psig with carbon monoxide gas at ambient temperature and heated and rocked until reaction temperature is reached, at which time additional carbon monoxide gas is added to increase the autoclave internal pressure to the predetermined value. Reactor pressure is maintained by adding carbon monoxide at the same rate at which it is consumed by the reactants. The carbon monoxide used is essentially pure. When the predetermined reaction time is completed the autoclave is cooled by a stream of cold air to approximately 25° C. After the gas is vented from the autoclave the crude product is analyzed by gas chromatographic methods. The % conversion is the mole percent of iodo-group converted to carboxylic acid. The results of these runs are shown below.

Obviously, numerous modifications and variations of the present invention are possible in light of the above teachings. It is therefore to be understood that within the scope of the appended claims, the invention may be practiced otherwise than as specifically described herein.

| Example No. 1 | |
|---|---|
| Iodoaromatic | p-Iodophenol |
| Weight (g) | 15.00 |
| Catalyst | Palladium Acetate |
| Weight (g) | 0.010 |
| Base | NaOH |
| Weight (g) | 2.80 |
| Carboxylic Acid/Water Mixture | Acetic Acid/Water |
| Weight (g) | 103.96/48.60 |
| Time (Hour) | 3 |
| Pressure (psig) | 1000 |
| Temperature (°C.) | 150 |
| % Conversion | 91.5 |
| Products (mmoles) | Phenol (5.34) |
| | p-Hydroxybenzoic Acid (57.27) |

| Example No. 2 | |
|---|---|
| Iodoaromatic | p-Iodophenol |
| Weight (g) | 15.00 |
| Catalyst | Palladium Acetate |
| Weight (g) | 0.010 |
| Base | LiOAc.2H$_2$O |
| Weight (g) | 7.00 |
| Carboxylic Acid/Water Mixture | Acetic Acid/Water |
| Weight (g) | 103.96/50.57 |
| Time (Hour) | 3 |
| Pressure (psig) | 1000 |
| Temperature (°C.) | 150 |
| % Conversion | 90.1 |
| Products (mmoles) | Phenol (5.89) |
| | p-Hydroxybenzoic Acid (53.70) |

| Example No. 3 | |
|---|---|
| Iodoaromatic | p-Iodophenol |
| Weight (g) | 15.00 |
| Catalyst | Palladium Acetate |
| Weight (g) | 0.010 |
| Base | NaOH |
| Weight (g) | 2.80 |
| Carboxylic Acid/Water Mixture | Acetic Acid |
| Weight (g) | 155.15 |
| Time (Hour) | 3 |
| Pressure (psig) | 1000 |
| Temperature (°C.) | 150 |
| % Conversion | 1.8 |
| Products (mmoles) | Phenol (17.09) |
| | p-Iodophenol (42.91) |
| | p-Hydroxybenzoic Acid (1.10) |

| Example No. 4 | |
|---|---|
| Iodoaromatic | p-Iodophenol |
| Weight (g) | 15.00 |
| Catalyst | Palladium Acetate |
| Weight (g) | 0.010 |
| Base | LiOAc.2H$_2$O |
| Weight (g) | 7.00 |
| Acid/Water Mixture | Acetic Acid |
| Weight (g) | 158.22 |
| Time (Hour) | 3 |
| Pressure (psig) | 1000 |
| Temperature (°C.) | 150 |
| % Conversion | 4.5 |
| Products (mmoles) | Phenol (16.36) |
| | p-Iodophenol (46.00) |
| | p-Hydroxybenzoic Acid (2.91) |

| Example No. 5 | |
|---|---|
| Iodoaromatic | p-Diiodobenzene |
| Weight (g) | 15.00 |
| Catalyst | Palladium Acetate |
| Weight (g) | 0.010 |
| Base | NaOH |
| Weight (g) | 2.80 |
| Carboxylic Acid/Water Mixture | Acetic Acid/Water |
| Weight (g) | 106.00/49.33 |
| Time (Hour) | 3 |
| Pressure (psig) | 1000 |
| Temperature (°C.) | 150 |
| % Conversion | 85.3 |
| Products (mmoles) | p-Diiodobenzene (5.58) |
| | p-Iodobenzoic Acid (2.21) |
| | Terephthalic Acid (37.66) |

| Example No. 6 | |
|---|---|
| Iodoaromatic | p-Diiodobenzene |
| Weight (g) | 15.00 |
| Catalyst | Palladium Acetate |
| Weight (g) | 0.010 |
| Base | NaOH |
| Weight (g) | 2.80 |
| Carboxylic Acid/Water Mixture | Acetic Acid |
| Weight (g) | 156.74 |
| Time (Hour) | 3 |
| Pressure (psig) | 1000 |
| Temperature (°C.) | 150 |
| % Conversion | 29.2 |
| Products (mmoles) | p-Diiodobenzene (25.11) |
| | p-Iodobenzoic Acid (11.44) |
| | Terephthalic Acid (8.90) |

-continued

Example No. 7

| | |
|---|---|
| Iodoaromatic | p-Iodoanisole |
| Weight (g) | 15.00 |
| Catalyst | Palladium Acetate |
| Weight (g) | 0.010 |
| Base | NaOH |
| Weight (g) | 2.80 |
| Carboxylic Acid/Water Mixture | Acetic Acid/Water |
| Weight (g) | 105.95/48.92 |
| Time (Hour) | 3 |
| Pressure (psig) | 1000 |
| Temperature (°C.) | 150 |
| % Conversion | 100 |
| Products (mmoles) | p-Anisic Acid (64.09) |

Example No. 8

| | |
|---|---|
| Iodoaromatic | p-Iodoanisole |
| Weight (g) | 15.00 |
| Catalyst | Palladium Acetate |
| Weight (g) | 0.010 |
| Base | NaOH |
| Weight (g) | 2.80 |
| Carboxylic Acid/Water Mixture | Acetic Acid |
| Weight (g) | 157.10 |
| Time (Hour) | 3 |
| Pressure (psig) | 1000 |
| Temperature (°C.) | 150 |
| % Conversion | 37.5 |
| Products (mmoles) | p-Iodoanisole (40.05) |
| | p-Anisic Acid (24.05) |

We claim:

1. A process for the production of an aromatic carboxylic acid which comprises carbonylating an iodoaromatic compound in the presence of carbon monoxide, a catalytic amount of palladium and a Bronsted base in a mixture of a carboxylic acid and water under aromatic carboxylic acid forming conditions of temperature and pressure.

2. The process of claim 1, wherein said iodoaromatic compound is selected from the group consisting of iodinated hydroxy, nitro, and aminoaromatic compounds.

3. The process of claim 1, wherein said iodoaromatic compound is p-iodophenol, p-diiodobenzene, 2,6-diiodonaphthalene, 4-iodo-2-phenylphenol, p-iodoaniline, or p-iodoanisole.

4. The process of claim 1, wherein said temperature is in the range of about 50° C. to 225° C.

5. The process of claim 4, wherein said temperature is in the range of about 100° C. to 175° C.

6. The process of claim 1, wherein said pressure is in the range of about 10 psig to 4000 psig.

7. The process of claim 6, wherein said pressure is in the range of about 300 psig to 1500 psig.

8. The process of claim 1, wherein said carbonylating step is conducted in the presence of an alkali or alkaline earth metal iodide.

9. the process of claim 8, wherein said alkali metal iodide is selected from the group consisting of lithium iodide, sodium iodide, potassium iodide, and rubidium iodide.

10. The process of claim 8, wherein said alkaline earth metal iodide is selected from the group consisting of magnesium diiodide, calcium diiodide, strontium diiodide, and barium diiodide.

11. The process of claim 1, wherein said Bronsted base is selected from the group consisting of acetates, formates, hydroxides, carbonates, and alkoxides of alkali and alkaline earth metals.

12. The process of claim 11, wherein said Bronsted base is an alkali metal carbonate.

13. The process for the production of a hydroxybenzoic acid which comprises carbonylating an iodophenol in the presence of carbon monoxide, lithium acetate, and a catalytic amount of a palladium in a mixture of acetic acid and water at a temperature of about 100° C. to 175° C. and a pressure of about 300 psig to 1500 psig.

14. A process for the production of p-hydroxy benzoic acid which comprises carbonylating p-iodophenol in the presence of carbon monoxide, lithium acetate, and a catalytic amount of palladium in a mixture of acetic acid and water at a temperature of about 175° C. and a pressure of about 750 psig.

* * * * *